United States Patent [19]

Bayard et al.

[11] 4,366,816
[45] Jan. 4, 1983

[54] COMBINATION QUICK DISCONNECT COUPLING AND FLUID CUTOFF VALVE

[75] Inventors: Michael A. Bayard, Chicago; James A. Turnbull, Grayslake, both of Ill.

[73] Assignee: Abbott Laboratories, North Chicago, Ill.

[21] Appl. No.: 219,016

[22] Filed: Dec. 22, 1980

[51] Int. Cl.³ .......................... A61J 7/00; A61M 1/00
[52] U.S. Cl. .............................. 128/213 A; 128/274; 251/149.5; 137/614.05
[58] Field of Search ............ 128/213, 214 R, 218 NV, 128/274; 137/614.05, 614.03; 251/149.5, 149.8, 149.9, 149.2, 149

[56] References Cited

U.S. PATENT DOCUMENTS

| | | | |
|---|---|---|---|
| 745,815 | 12/1903 | Gibson . | |
| 808,446 | 12/1905 | Gill et al. | |
| 968,711 | 8/1910 | Stevenson . | |
| 1,580,312 | 4/1926 | Long . | |
| 2,275,477 | 3/1942 | Sundholm | 251/149.8 |
| 2,502,206 | 3/1950 | Creek | 251/149.1 |
| 2,779,608 | 1/1957 | Abbey | 251/149.1 |
| 3,588,149 | 6/1971 | Demler et al. | 285/110 |
| 3,626,980 | 12/1971 | Svensson | 251/149 X |
| 3,876,234 | 4/1975 | Harms | 285/38 |
| 4,019,512 | 4/1977 | Tenczar | 128/214 R |
| 4,022,205 | 5/1977 | Tenczar | 128/214 R |
| 4,030,494 | 6/1977 | Tenczar | 128/214 R |
| 4,046,145 | 9/1977 | Choksi et al. | 128/215 |
| 4,055,179 | 10/1977 | Manschot et al. | 128/275 |
| 4,056,116 | 11/1977 | Carter et al. | 137/68 R |
| 4,076,285 | 2/1978 | Martinez | 285/332 |
| 4,080,965 | 3/1978 | Phillips | 128/214 D |
| 4,133,312 | 1/1979 | Burd | 128/214 |
| 4,161,949 | 7/1979 | Thanawalla | 128/247 |
| 4,186,752 | 2/1980 | Guerra | 128/766 |
| 4,187,846 | 2/1980 | Lolachi et al. | 128/214 R |
| 4,201,406 | 5/1980 | Dennehey et al. | 285/3 |

FOREIGN PATENT DOCUMENTS 2809303  3/1978  Fed. Rep. of Germany .

*Primary Examiner*—Stephen C. Pellegrino
*Attorney, Agent, or Firm*—Robert S. Beiser; Robert L. Niblack

[57] ABSTRACT

A combination quick disconnect coupling and fluid cutoff valve particularly adapted for use in continuous ambulatory peritoneal dialysis comprises a first tubular member connected to a length of flexible tubing and having a fluid passageway therethrough, and a second tubular member connected to a second length of flexible tubing and constructed for telescopic reception of the first tubular member. A rotatable sleeve is disposed within the first tubular member (partially closed at a first end). By rotating the sleeve the fluid passageway may be selectively opened or closed. A coupling mechanism, such as a bayonet lock is used for retaining the first and second tubular members together. A series of lugs extend inwardly from the second tubular member and are arranged to engage the rotatable sleeve as the first tubular member is inserted into the second tubular member, so as to advance the movable sleeve to an open position during coupling thereby opening the fluid passageway. Finally, a resilient sealing mechanism is used for hermetically sealing the connection between the first and second members.

15 Claims, 8 Drawing Figures

COMBINATION QUICK DISCONNECT COUPLING AND FLUID CUTOFF VALVE

BACKGROUND OF THE INVENTION

The present invention relates generally to the field of connector mechanisms for fixedly joining together the ends of two pieces of flexible tubing in a manner which is disengageable, but which resists accidental disconnection. Connectors of this general type are capable of a wide variety of uses, but are particularly useful in forming fluid connections between pieces of flexible tubing utilized in a wide variety of medical and surgical devices in hospitals and similar environs. The connector or coupling of the present invention was developed specifically for use in continuous ambulatory peritoneal dialysis.

Prior to the present invention, connectors of this general type have been used for many years to effectuate rapid and effective junctions between pieces of tubing. A requirement of such connectors is that a fluid tight seal be obtained. Another requirement is that the connection, once made, should be strongly resistant to inadvertent disengagement, but should be readily disengageable when desired by simple and rapid manual manipulation.

Exemplary of prior art coupling devices or valves used in medical applications are the following U.S. patents:

U.S. Pat. No. 4,055,179—Valve for Urinary Drainage Container or Similar Article—James Gordon Manschot, et al.—granted 10/25/77;

U.S. Pat. No. 3,588,149—Vacuum or Pressure Coupling Devices—Henry William Demler, Sr., et al.—granted 6/28/71;

U.S. Pat. No. 4,046,145—Syringe Connector—Pradip Vinobchandra Choksi, et al.—granted 9/6/77;

U.S. Pat. No. 3,876,234—Twist-Lock Connector—Jack L. Harms—granted 4/8/75;

U.S. Pat. No. 4,133,312—Connector for Attachment of Blood Tubing to External Arteriovenous Shunts and Fistulas—Samuel Burd—granted 1/9/79;

Method and Apparatus for Continuous, Ambulatory Peritoneal—Robert P. Popovich—Abandoned.

U.S. Pat. No. 4,161,949—Aseptic Connector—Chandrakant B. Thanawalla—granted 7/24/79;

U.S. Pat. No. 4,019,512—Adhesively Activated Sterile Connector—Francis J. Tenczar—granted 4/26/77;

U.S. Pat. No. 4,056,116—Valve for Interconnecting Sterile Containers and the Like—Garry L. Carter, et al.—granted 11/1/77;

U.S. Pat. No. 4,080,965—In-Line Cannula Valve Assembly—Thomas E. Phillips—granted 3/28/78;

U.S. Pat. No. 4,022,205—Fluid Connectors—Francis J. Tenczar—granted 5/10/77;

U.S. Pat. No. 4,076,285—Laminar Flow Connector for Conduits—Felix Jesus Martinez—granted 2/28/78;

U.S. Pat. No. 4,030,494—Fluid Connectors—Francis Tenczar—granted 6/21/77;

U.S. Pat. No. 4,201,406—Spike Connector for Solution Bag—T. Michael Dennehey—granted 5/6/80;

U.S. Pat. No. 745,815—Hose-Coupling—William W. Gibson—granted 12/1/03;

U.S. Pat. No. 808,446—Coupling—L. D. Gill, et al.—granted 12/26/05;

U.S. Pat. No. 4,186,752—Device for Taking Blood and For Injecting Medication—Luis A. Guerra—granted 2/5/80;

U.S. Pat. No. 1,580,312—Combined Plug Valve and Hose Connection—J. F. Long—granted 4/13/26;

U.S. Pat. No. 968,711—Hydrant—J. W. Stevenson—granted 8/30/10.

In the field of peritoneal dialysis, a relatively high rate of peritonitis has been found. It is suspected that this is due to the passage of microorganisms through the connecting mechanism utilized, and hence into the peritoneal cavity of the patient. In order to prevent such microbial contamination, it is an advantage of the present invention to provide a combination quick disconnect coupling and fluid cutoff valve, which prevents access to the peritoneal cavity except when both halves of the coupling are engaged. It is an additional advantage of the present invention to provide such a coupling mechanism which is relatively easy to manipulate and inexpensive to manufacture.

SUMMARY OF THE INVENTION

The foregoing advantages are accomplished and the shortcomings of the prior art are overcome by the combination quick disconnect coupling and fluid cutoff valve of the present invention, which comprises two tubular members each having a fluid passage therethrough. Each tubular member is connected to a length of flexible tubing. The second tubular member is constructed for telescopic reception of the first tubular member. A coupling mechanism, preferably in the form of a bayonet lock, engages and relates the tubular members together. A movable sleeve disposed within the first tubular member serves as the valving mechanism. The sleeve is partially closed at one end and the flow can be controlled by selectively opening or closing that end of the fluid passageway. A series of lugs extend either from the second tubular member or alternatively from the second end of the sleeve. The lugs are constructed and arranged for engagement with a series of corresponding slots integrally formed in the second end of the sleeve or, alternatively, in the second tubular member. The lugs are designed to advance the movable sleeve to an open position, when the first and second tubular members are coupled together. This opens the fluid passageway and thus acts as a valve. A resilient sealing mechanism between the first and second tubular members hermetically seals the connection therebetween.

The partially closed end of the rotating sleeve preferably includes an aperture therethrough which is adapted for the passage of liquid, upon alignment with a corresponding aperture in the first end of the first tubular member. Alternatively, when the two apertures are out of alignment, liquid flow is halted. The alignment takes place upon advancement of the movable sleeve.

As an additional feature of the invention, a tubular male fitment may be disposed within the second tubular member. The fitment has an aperture extending therethrough, and is constructed so as to be telescopically received by the first tubular member upon joinder of the first and second tubular members. Essentially, the male fitment comprises a Luer lock mechanism.

The coupling mechanism preferably comprises a bayonet lock. A plurality of lugs extend from the exterior of the second tubular member and are adapted for locking engagement with a series of shoulders disposed about the first tubular member. Thus, the first and second tubular members are longitudinally joined and then rotated in the opposite direction so as to engage the shoulders of the first tubular member in front of the lugs of the second tubular member, thereby preventing longitudinal movement of either member.

The previously mentioned resilient sealing mechanism preferably comprises a toric elastomeric sealing member or O-ring, circumscribed about, attached to and extending from, the male fitment mechanism. Thus, when the first and second tubular members are joined, the male fitment causes a hermetic seal between the O-ring and the interior of the first tubular member.

Alternatively, or in addition thereto, a toric elastomeric sealing member may be disposed within and attached to the rotating sleeve, for hermetically sealing the connection between the male fitment and the interior of the rotating sleeve. An additional alternative is the inclusion of a number of resilient sealing members between the rotating sleeve and the first member. These may be positioned either proximate the second end of the first tubular member, proximate the middle of the first tubular member and about its interior, or between the first end of the rotating sleeve and the first end of the first tubular member. When a resilient sealing member is disposed between the first end of the rotating sleeve and the first end of the first tubular member, an aperture is required to allow the passage of liquid through the device.

As previously noted, a second sealing member may be disposed between the second end of a movable sleeve and the interior of the second tubular member. In this and several of the previous cases, the resilient sealing mechanism comprises a plurality of foam pads impregnated with an antimicrobial agent, such as Betadine. Alternatively, the resilient sealing mechanism may comprise a rubber washer or gasket. Since the coupling device is designed generally for use in medical applications, and particularly for use with peritoneal dialysis, both the materials selected and the configuration of the device are sterilizable and sterility maintaining. As a result, a sterile connection can be maintained when the first and second tubular members are joined in a sterile condition.

The present invention is particularly useful in continuous ambulatory peritoneal dialysis where a series of dialysate solution bags are connected to the catheter within the patient. Initially, dialysate solution is drained into the peritoneum. An ambultory period then occurs during which body wastes are transmitted by osmosis action through the peritoneum and into the dialysate. After a sufficient period of time, spent dialysate is drawn by gravity from the patient into an empty container. A new dialysate solution is then drained into the peritoneum. During the ambulatory period between exchange of solutions, a protective cap may be attached to the first tubular member so as to facilitate movement by the patient.

In the present invention, a cap may be attached to the first tubular member after removal of the second tubular member, for hermetic sealing thereof. The cap includes a coupling mechanism proximate its distal end, adapted for engagement with the coupling means of the first tubular member. The cap further includes a resilient antiseptic plug coaxially disposed therein, and adapted for telescopic reception by and sealing of the second end of the first tubular member.

As previously mentioned, both the first and second tubular members have lengths of flexible tubing attached thereto. One means of such attachment is the use of barbed fitments about the periphery of a port extending from each of the tubular members. These barbed fitments are constructed and arranged for a telescopic insertion into and engagement with the flexible tubing, thereby fixedly attaching the flexible tubing to the port.

A BRIEF DESCRIPTION OF THE DRAWINGS

FIG. 1 of the drawings is a front perspective view of an improved quick disconnect coupling and fluid cutoff valve.

FIG. 1A of the drawings is a front perspective view of the quick disconnect coupling of FIG. 1 shown in a disassembled configuration.

FIG. 2 of the drawings is a vertical section of the coupling device of FIG. 1.

FIG. 3 of the drawings is a vertical section of the coupling device of FIG. 2 shown separated into first and second tubular members.

FIG. 4 of the drawings is a vertical section of the first tubular member of FIG. 3 with a protective cap member attached to the first tubular member.

FIG. 5 of the drawings is a vertical section of the first tubular member and protective cap of FIG. 4, shown in a separated configuration.

FIG. 6 of the drawings is a vertical section of an alternative embodiment of the first tubular member of FIGS. 1 through 5.

FIG. 7 of the drawings is a vertical section of an additional alternative embodiment of the first tubular member of FIGS. 1 through 5.

DETAILED DESCRIPTION OF THE PREFERRED EMBODIMENT

Figure 1:
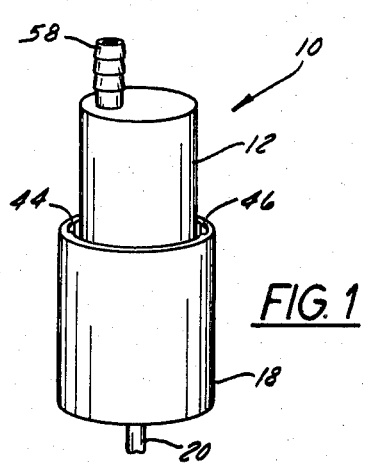
Figure 1A:
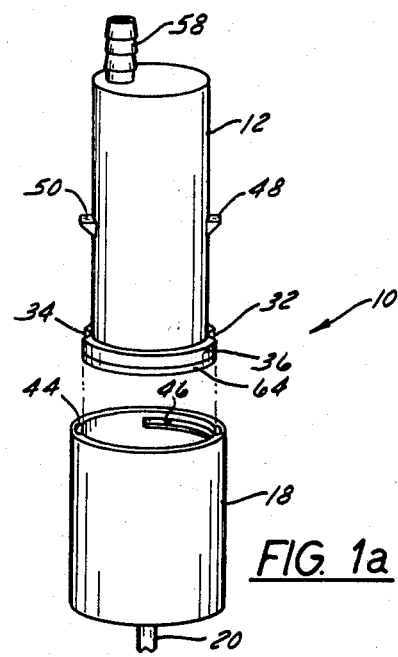

While this invention is susceptible of embodiment in many different forms, there is shown in the drawings and will herein be described in detail several specific embodiments, with the understanding that the present disclosure is to be considered as an exemplification of the principles of the invention and is not intended to limit the invention to the embodiments illustrated.

Figure 2:
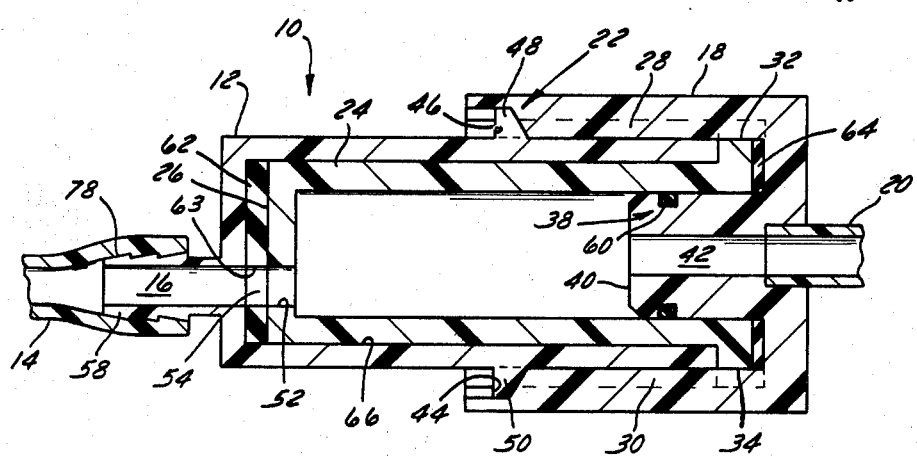

As best seen in FIG. 2 of the drawings, combination quick disconnect coupling and fluid cutoff valve 10 comprises a first tubular member 12 connected to a length of flexible tubing 14 and having fluid passageway 16, extending therethrough. Second tubular member 18 is connected to flexible tubing 20 and is constructed and arranged for telescopic reception of first tubular member 12. Coupling mechanism 22, in the form of a bayonet lock, to be explained later, shown in an engaged configuration, retains first tubular member 12 in compressive engagement to second tubular member 18. Movable sleeve 24 is disposed within first tubular member 12 and is partially closed at first end 26, so as to allow selective opening or closing of fluid passageway 16.

Figure 3:
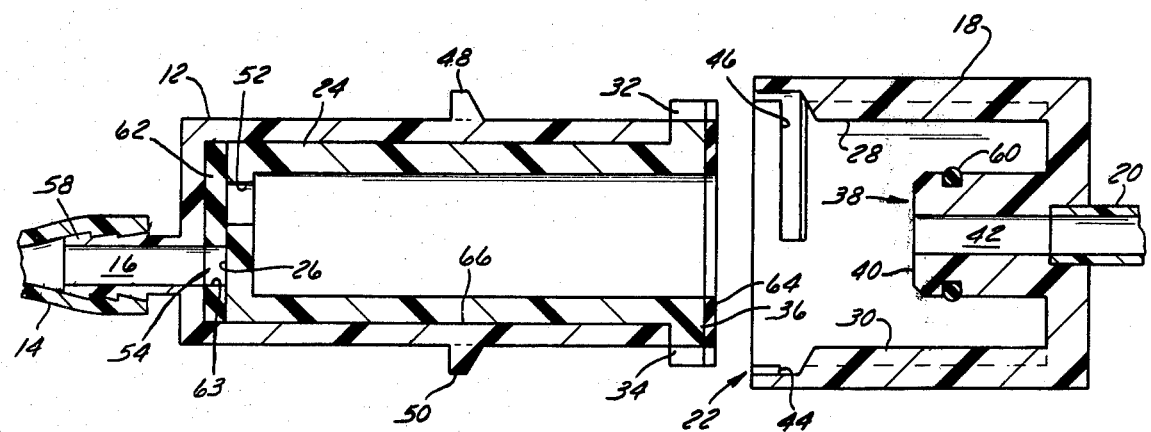
Figure 4:
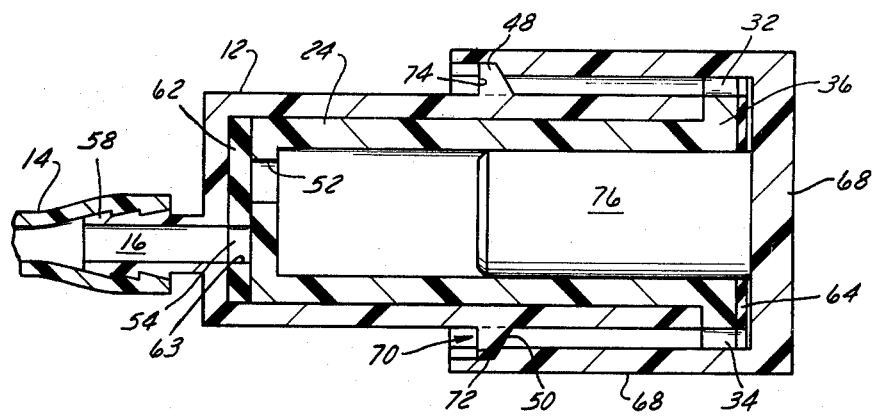

As best seen in FIG. 3, lug members 28 and 30 extend inwardly from second tubular member 18 and are constructed and arranged for engagement with corresponding slots 32 and 34, integrally formed in second end 36 of movable sleeve 24. Alternatively, lugs 28 and 30 may be integrally formed and extend from first tubular member 12, and engage corresponding slots 32 and 34 formed in the interior of second tubular member 18.

Lug members 28 and 30 effectively advance movable sleeve 24 to an open position when first tubular member 12 is held stationary and second tubular member 18 is rotated. In the embodiment shown, when second tubular member 18 is rotated to a locked position, lugs 28 and 30 abut against slots 32 and 34 and cause rotation of movable sleeve 24, so as to open fluid passageway 16. Resilient sealing mechanism 38 hermetically seals the connection between first tubular member 12 and second tubular member 18.

As further seen in FIG. 3 of the drawings, coupling mechanism 22 is shown as a bayonet lock comprising lug members 44 and 46 extending inwardly from second tubular member 18 and adapted for locking engagement with shoulders 48 and 50 disposed on first tubular member 12. Thus, first tubular member 12 is telescopically inserted into second tubular 18 until lugs 44 and 46 are past shoulders 48 and 50. Second tubular member 18 is then rotated until lugs 44 and 46 are in abutment with and engaged against the shoulders. Longitudinal movement of first tubular member 12 or second tubular member 18 is thereby prevented.

As also seen in FIG. 3, in a preferred embodiment, second tubular member 18 includes tubular male fitment 40 having aperture 42 extending therethrough. Male fitment 40 is disposed within second tubular member 18 and is sized and positioned so as to be telescopically received by sleeve 24 in first tubular member 12.

Returning to FIG. 2, partially closed end 26 of movable sleeve 24 includes aperture 52 extending therethrough. When movable sleeve 24 is rotated so that aperture 52 is in alignment with aperture 54, formed in first end 56 of first tubular member 12, liquid may flow from the interior of movable sleeve 24 through apertures 52 and 54 and out of fluid passageway 16.

Figure 6:
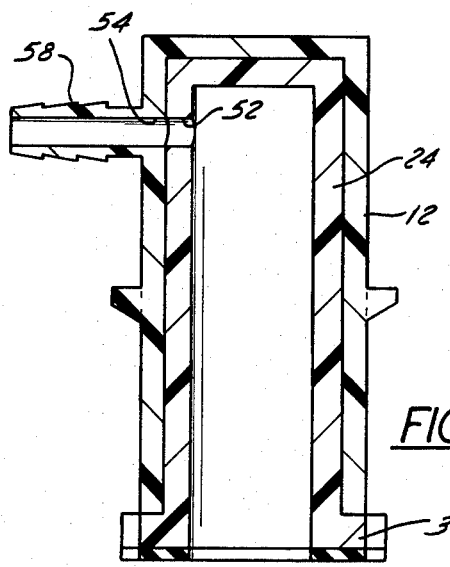
Figure 7:
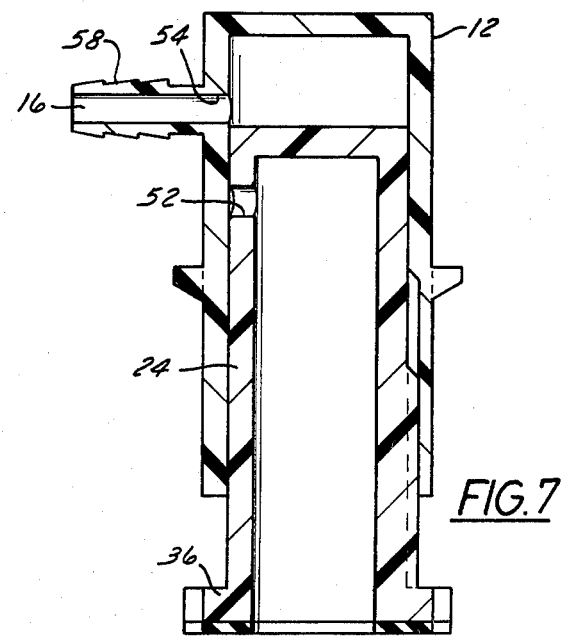

Alternatively, as best seen in FIGS. 6 and 7 of the drawings, aperture 52 may be positioned on the side of movable sleeve 24. Aperture 54 in port 58 is correspondingly disposed sidewardly from first tubular member 18. In order to align aperture 52 with aperture 54, in the embodiment shown in FIG. 6, movable sleeve 24 may be rotated. Alternatively, as seen in FIG. 7, in order to align aperture 52 with aperture 54, movable sleeve 24 may be slidably moved within first tubular member 12. In this embodiment, when second tubular member 18 engages against second end 36 of movable sleeve 24, sleeve 24 slides forward until aperture 52 is in alignment with aperture 54. Fluid passage 16 is thereby opened.

As further seen in FIGS. 2 and 3 of the drawings, resilient sealing means 38 comprises a toric elastomeric sealing member or O-ring 60, attached to and extending from male fitment 40. When male fitment 40 is compressively engaged into movable sleeve 24, O-ring 60 hermetically seals the connection between first member 12 and second member 18.

Additionally shown are resilient sealing members 62, 64 and 66 which are disposed between movable sleeve 24 and first member 12 or second member 18. In the embodiment shown, resilient sealing member 62 disposed at first end 56 of first tubular member 12 includes an aperture 62 which allows the passage of liquid when aperture 52 is in alignment with aperture 54 of first tubular member 12. Resilient sealing means 62, 64 and 66 preferably comprise foam pads impregnated with an antimicrobial agent such as betadine. It should be noted that O-ring 60 may be attached to movable sleeve 24 rather than male fitment 40, and still accomplish the same function. Along these same lines, in order to be useful in medical applications, coupling device 10 is constructed of a sterilizable material such as polyethylene, polypropylene, polycarbonate, polyvinylchloride, acrylonitrile butadiene, styrene, or other commonly known plastic materials which may withstand sterilization. In addition, because of resilient sealing means 38, if first tubular member 12 and second tubular member 18 are joined in a sterile condition, the hermetic seal created by resilient sealing means 38 maintains the sterile condition within connector 10. While resilient sealing mechanism members 60, 62, 64 and 66 may comprise a foam pad, commonly known elastomeric washers or gaskets shaped to conform to the tubular member being sealed may also be used.

Figure 5:
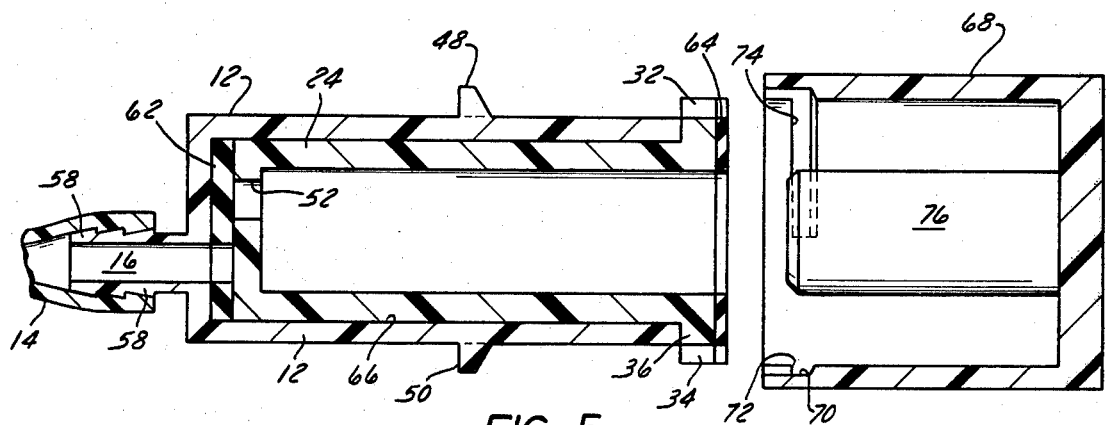

When second tubular member 18 is disconnected from first tubular member 12, some means must be found for sealing the interior of movable sleeve 24, so as to prevent microbial contamination. In order to accomplish this, and also to prevent the ingress of particulate matter, as best seen in FIG. 5, protective cap 68 is provided. Protective cap 68 hermetically seals first tubular member 12 and includes coupling mechanism 70, which comprises lugs 72 and 74. Lugs 72 and 74 are adapted for engagement against shoulders 48 and 50 of first tubular member 12, so as to compressively engage cap 68 against first tubular member 12, when cap 68 is joined to first tubular member 12. Protective cap 68 further includes resilient antiseptic plug 76 coaxially disposed within protective cap 68 and adapted in size and configuration for telescopic reception by and the sealing of the second end 36 of first tubular member 12. In a preferred embodiment, antiseptic plug 76 comprises a resilient foam material impregnated with an antimicrobial agent, such as betadine.

As previously mentioned, first tubular member 12 is connected to flexible tubing 14 and second tubular member 18 is connected to flexible tubing 20. One means of accomplishing such connection is the use of barbed fitments 78, as seen in FIG. 2, disposed about port 58. The outside diameter of port 58 and fitment 78 is such that it may be telescopically received by flexible tubing 14 and engaged therein for fixed attachment.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim:

1. A combination quick disconnect coupling and liquid cutoff valve for continuous ambulatory peritoneal dialysis comprising:
   a first tubular member connected to a length of flexible tubing and having a fluid passageway therethrough;
   a second tubular member connected to a length of flexible tubing and constructed and arranged for telescopic reception of said first tubular member;
   movable sleeve means disposed within said first tubular member, partially closed at a first end portion, for the selective opening or closing of said fluid passageway; and
   means for selective movement of said movable sleeve;
   a first resilient sealing member disposed between the first end of said movable sleeve means and the first end of said first tubular member, said resilient sealing member having an aperture adapted for the selective passage of liquid therethrough when in alignment with said fluid passageways of said movable sleeve and said first tubular member.

2. A combination quick disconnect coupling and liquid cutoff valve for continuous ambulatory peritoneal dialysis comprising:
- a first tubular member connected to a length of flexible tubing and having a fluid passageway therethrough;
- a second tubular member connected to a length of flexible tubing and constructed and arranged for telescopic reception of said first tubular member;
- movable sleeve means disposed within said first tubular member, partially closed at a first end portion, for the selective opening or closing of said fluid passageway;
- means for selective movement of said movable sleeve means;
- coupling means for the selective engagement and retention of said first tubular member to said second tubular member;
- said coupling means comprising a bayonet locking mechanism having a plurality of lug members extending inwardly from said second tubular member, constructed and arranged for locking engagement with a plurality of shoulder members disposed about said first tubular member, thereby fixedly positioning said first and second tubular members together in compressive engagement;
- a first resilient sealing member disposed between said first end of said movable sleeve means and the first end of said first tubular member, said resilient sealing member having an aperture adapted for the selective passage of liquid therethrough when in alignment with said fluid passageways of said movable sleeve means, and said first tubular member.

3. The coupling device as disclosed in claim 1 or 2 wherein said means for selective opening or closing of said fluid pathway comprises a plurality of lug members extending inwardly from said second tubular member constructed and arranged for engagement with a plurality of corresponding slots integrally formed in said second end of said sleeve means, said lug members being effective to advance said movable sleeve means to an open position upon coupling of said first and second tubular members, thereby opening said fluid passageway.

4. The invention according to claim 1 or 2 and further including resilient sealing means between said first and second tubular members for hermetically sealing the connection therebetween.

5. The coupling device as disclosed in claim 1 or 2 wherein said movable sleeve means comprises a slidable sleeve member constructed and arranged for the passage of liquid therethrough upon the advancement of said slidable sleeve member to an open position.

6. The coupling device as disclosed in claim 1 or 2 wherein said means for selective opening and closing of said fluid pathway comprises:
- a plurality of lug members extending inwardly from the second end of said sleeve means constructed and arranged for engagement with a plurality of corresponding slots integrally formed in said second tubular member, said lug members being effective to advance said movable sleeve means to an open position upon coupling of said first and second tubular members, thereby opening said fluid passageway.

7. The coupling device as disclosed in claim 1 or 2 wherein said movable sleeve means comprises a rotatable sleeve member constructed and arranged for the passage of liquid therethrough upon the rotation of said rotatable sleeve member to an open position.

8. The coupling device as disclosed in claim 7 and further including tubular male fitment means having an aperture therethrough and disposed within said second tubular member, said tubular male fitment means being constructed and arranged for telescopic reception by said movable sleeve member.

9. The coupling device as disclosed in claim 8 wherein said resilient sealing means comprises a toric elastomeric sealing member circumscribed about, attached to and extending from said male fitment means for the hermetic sealing of the connection between said male fitment means and the interior of said first tubular member.

10. The coupling device as disclosed in claim 8 wherein said resilient sealing means comprises a toric elastomeric sealing member disposed within and attached to said movable sleeve member for the hermetic sealing of the connection between said male fitment means and the interior of said rotating sleeve member.

11. The coupling device as disclosed in claim 7 wherein said resilient sealing means comprises a plurality of resilient sealing members disposed between said movable sleeve means and said first member or second tubular members.

12. The coupling device as disclosed in claim 7 wherein a second sealing member is disposed between the second end of said movable sleeve means and the interior of said second tubular member for the hermetic sealing thereof and further including resilient sealing means between said first and second tubular members.

13. The coupling device as disclosed in claim 2 wherein said resilient sealing means comprises a plurality of foam pad members impregnated with an antimicrobial agent such as povidone iodine.

14. The coupling as disclosed in claim 2 or 13 wherein said coupling device is sterilizable and sterility maintaining when said first tubular member and said second tubular members are joined in a sterile condition.

15. The coupling as disclosed in claim 2 and further including;
- a protective cap member adapted for engagement with and hermetic sealing of said first tubular member, said protective cap member comprising coupling means proximate its distal end and adapted for engagement with said movable sleeve means in said first tubular member; and
- a resilient antiseptic plug member coaxially disposed therein and adapted for telescopic reception by and the sealing of the second end of said first tubular member.

* * * * *